United States Patent [19]

Homma et al.

[11] Patent Number: 4,612,303

[45] Date of Patent: Sep. 16, 1986

[54] THERAPEUTIC AND/OR PREVENTIVE AGENT FOR OBSTRUCTIVE RESPIRATORY DISEASES

[75] Inventors: Naoshi Homma, Tochigi; Jin Sato, Tokorozawa, both of Japan

[73] Assignee: Eisai Co., Ltd., Tokyo, Japan

[21] Appl. No.: 611,068

[22] Filed: May 17, 1984

[30] Foreign Application Priority Data

May 23, 1983 [JP] Japan .................................. 58-89067

[51] Int. Cl.$^4$ ............................................. A61K 31/70
[52] U.S. Cl. ...................................................... 514/23
[58] Field of Search ................... 424/180; 536/4.1; 514/23

[56] References Cited
U.S. PATENT DOCUMENTS 4,247,540  1/1981  Holzmann ............................. 424/95

FOREIGN PATENT DOCUMENTS 0129093  12/1984  European Pat. Off. .............. 514/23

OTHER PUBLICATIONS

Tomaska et al., Inhibition of Secondary IgG Responses by N-Acetyl-D-Galactosamine, Eur J Immunol 11, 181–86, (1981).
Nicosia, Lectin-Induced Mucus Release . . . , Science 206,698 (1979).
Last et al., Mucus Glycoprotein Secretion by Tracheal Explants . . . , Chem. Abstracts 93: 180528e, (1980).
Morris, Enzymic Assay for Submolar Amounts of L-Fucose, Chem. Abstracts, 97: 3027c, (1982).

*Primary Examiner*—Ethel G. Love
*Attorney, Agent, or Firm*—Flynn, Thiel, Boutell & Tanis

[57] ABSTRACT

A remedial or prophylactic agent for the treatment of obstructive respiratory diseases comprises a therapeutically effective amount of L-fucose.

7 Claims, No Drawings

THERAPEUTIC AND/OR PREVENTIVE AGENT FOR OBSTRUCTIVE RESPIRATORY DISEASES

This invention relates to a novel therapeutic and/or preventive agent for obstructive respiratory diseases. More particularly, the invention relates to a therapeutic and/or preventive agent for obstructive respiratory diseases which comprises L-fucose as an active ingredient.

Xanthine compounds such as theophylline, beta-receptor stimulants such as epinephrine (adrenaline) or ephedrine, alpha-block-agents, disodium cromoglycate compounds, Ca-suppressors and steriods have been conventionally used for treating various obstructive respiratory diseases represented by bronchial asthma. However, the fact is that there has been no fully satisfactory pharmaceutical for treating such obstructive respiratory diseases. For example, bronchodilators such as xanthine compounds or β-receptor stimulants stimulate the cardiovascular system to thereby increase heart rate and myocardial oxygen consumption. Accordingly these pharmaceuticals are unsuitable for patients suffering from cardiovascular disorders such as hyperpiesia or ischemic heart disease.

On the other hand, it is sometimes difficult to withdraw steriods, which would result in an increase in the mortality from recurrent obstructive respiratory diseases such as bronchitis.

Under these circumstances, we have tried to find a pharmaceutical available for a complete treatment of various respiratory obstructions represented by bronchial asthma. Pursuing an unknown cause lying behind various causes of asthma, we have found that the respiratory obstructions represented by bronchial asthma may be caused by the absence of L-fucose which is a methylose and corresponds to 6-deoxy-L-galactose. We have further pursued this compound and found that L-fucose might be remarkably effective for treating and/or preventing respiratory obstructions in various clinical observations.

Accordingly, it is an object of the present invention to provide a novel therapeutic and/or preventive agent for treating respiratory obstruction.

L-Fucose to be used in the present invention is a methyl sugar and corresponds to 6-deoxy-L-galactose. It occurs as a constituent of cell walls of seaweeds or of blood group polysaccharides of animal.

L-Fucose to be used in the present invention may be prepared by any method. For example it may be prepared by hydrolyzing brown algae with an acid followed by neutralization, fermenting it with galactose fermentation yeast, removing mannose and galactose, extracting with an alcohol after concentration and separating as difficulty soluble phenylhydrazine.

α-L-Fucose melts at 140° C. and exhibits mutarotation.

The term "respiratory obstruction" as used herein means pathosis accompanied by intensified respiratory resistance, such as recurrent obstructive bronchitis including asthma or chronic obstructive bronchitis.

Now the reason why L-fucose of the present invention is effective for treating and/or preventing respiratory obstruction will be described.

Type I allergy is considered to be a result of the bonding of immunoglobulin E (IgE) to membranes on the surface of mast cells or basophilic leucocytes. Further it is known that IgE would be liable to be affected by lectin having specificity against a fucose residue such as Lotus Tetragonolobus Agglutinin (bird's foot trefoil agglutinin), Lotus A, or Ulex Europeus Agglutinin (furze agglutinin), UEA-1, when bonding to these cell membranes by an antigenic stimulation. Lectin is also called hemagglutinin or phytohemagglutinin and occurs not only in plants but also in animals and microorganisms. Various alien substances represented by pathogenic microorganisms invading a vital body (generically called lectins) would not directly fix to the target tissue but exhibit a mutual interaction with a substance in humors, if any, showing an affinity for lectins to inhibit the affinity for the target tissue, thereby protecting the vital body.

On the basis of the aforementioned theory, L-fucose, showing an affinity for lectins which have specificity against L-fucose and contain a fucose residue in a receptor group, such as UEA-1 or Lotus A, is administered to treat and prevent obstructive respiratory diseases according to the invention.

Accordingly the present invention provides a pharmaceutical composition comprising L-fucose which would affect the mutual interaction between IgE and mast cells or basophilic leucocytes to thereby treat and/or prevent obstructive respiratory diseases.

To further illustrate the effect of the pharmaceutical composition of the present invention, the following clinical examples are given.

CLINICAL EXAMPLE 1

A male patient of 12 years old, suffering from bronchial asthma and atopy:

Before administration, the patient suffered from serious bronchial asthma accompanied with atopy. The disease was perennial and an attack was observed once or twice a month. Each attach continued for several days to a week. A steroid was mainly administered as a remedy, but the condition of the patient was not improved.

α-L-Fucose, the compound of the present invention, was administered to him by inhalation in a dose of 20 mg. The inhalant was prepared by dissolving α-L-fucose in a physiological saline solution.

α-L-Fucose was administered by inhalation once a week or every other week in a dose of 20 mg. Five weeks after the initiation of the administration, the patient had no attack. In addition he had no stridor after two months.

CLINICAL EXAMPLE 2

A female patient of six years old, suffering from bronchial asthma:

It was a mild case of bronchial asthma. The main symptom of the patient was wheezing. She suffered from attacks three or four times a year. α-L-Fucose was administered to her by inhalation in a dose of 15 mg once a week in a similar manner to Clinical Example 1. Three weeks after the initiation of the administration, the patient had no stridor. She had been in a good condition for four months except temporary stridor caused by common cold.

CLINICAL EXAMPLE 3

A female patient of nine years old, suffering from chronic obliterative bronchitis:

α-L-Fucose was administered to the patient having wheezing and respiratory resistance in a dose of 15 mg once a week. Three weeks after the initiation of the administration, the wheezing and respiratory resistance were improved. By further administration, she has been in a good condition for five months with no wheezing nor respiratory resistance except temporary stridor (twice) caused by common cold.

L-Fucose, which is the compound of the present invention, may be administered safely since it is scarcely toxic.

Speaking more concretely, α-L-fucose was administered to CDF male mice of thirty weeks of age intravenously, intraperitoneally and orally (each group contained 10 mice) for eight days to determine or observe the body weights, behaviors and the like. Consequently neither abnormal symptoms, abnormal behavior nor decrease in body weight were observed at all. In addition, biochemical examinations on blood collected on the final day showed no abnormality.

Clinical Examples 1, 2 and 3 as described above obviously suggest that the compound of the present invention, i.e., L-fucose, would be highly effective for treating respiratory obstruction. Therefore the present invention has proved of great value since it provides an effective therapeutic pharmaceutical for respiratory obstruction represented by asthma.

The compound of the present invention, i.e. L-fucose, may be administered orally including inhalation or parenterally, e.g., subcutaneously or intravenously, as a therapeutic and/or preventive agent for respiratory obstruction. It is administered in a dose generally from approximately 10 to 300 mg and preferrably from 40 to 60 mg to an adult depending on diseases, the degree of symptoms, age, body weight, simultaneous treatments, if any, or the like.

The compound of the present invention may be formulated into conventional pharmaceutical forms such as a tablet, granules, powder, inhalant, injection, suppository, aerosol or spray.

In the case of the formulation of a solid pharmaceutical for oral administration, an excipient and, if desired, a binder, a disintegrant, a lubricant, a flavor or the like are added to the active compound to obtain tablets, coated tablets, granules, powder, capsules or the like.

Examples of excipients are lactose, corn starch, refined sugar, glucose, sorbitol and crystalline cellulose. Examples of binders are polyvinyl alcohol, polyvinyl ether, ethylcellulose, methylcellulose, gum arabic, tragacanth, gelatin, shellac, hydroxypropylcellulose, hydroxypropylstarch and polyvinylpyrrolidone. Examples of disintegrants are starch, agar, powdery gelatin, crystalline cellulose, calcium carbonate, sodium hydrogencarbonate, calcium citrate, dextrin and pectin. Examples of lubricants are magnesium stearate, talc, polyethylene glycol, silica and hardened vegetable oils. Colorants approved as additives to pharmaceutical compostions may also be added. Examples of flavors are powdery cacao, menthol, aroma acids, mentha oil, borneol and powdered cinnamon bark. These tablets or granules may be coated with sugar or gelatin or any desired coating if necessary.

In the case of the formulation of an injection, a pH adjustor, a buffer, a stabilizer, a preservatives etc. are added to the active compound, if necessary, to prepare a hypodermic or intravenous injection in a conventional manner.

In the case of the formulation of an inhalation, the active compound is treated in a conventional manner. More particularly, a sufficient amount, e.g. 0.2 to 0.5 ml (preferably 0.3 to 0.4 ml) for a child and 0.3 to 2 ml (preferably 0.6 to 1 ml) for an adult, of a 5% α-L-fucose solution is dissolved in 0.7 to 3 ml of a physiological saline solution and charged into an inhalator.

An inhalation aerosol may be prepared in a conventional manner by the use of fluorocarbons as a propellant.

The embodiments of the invention in which an exclusive property or privilege is claimed are defined as follows:

1. A method for treating and preventing bronchitis and asthma which comprises administering to a human patient afflicted with bronchitis or asthma, a pharmaceutical composition consisting essentially of a therapeutically effective amount of L-fucose, as the only active ingredient, in combination with a pharmaceutically acceptable carrier.

2. A method as claimed in claim 1, in which said L-fucose is alpha-L-fucose.

3. A method as claimed in claim 1 in which said pharmaceutical composition is administered by inhalation.

4. A method as claimed in claim 1 in which said pharmaceutical composition is administered subcutaneously.

5. A method as claimed in claim 1 in which said pharmaceutical composition is administered intravenously.

6. A method as claimed in claim 1 in which said pharmaceutical composition is administered orally.

7. A method as claimed in claim 1 in which said therapeutically effective amount of L-fucose is from 10 to 300 mg.

* * * * *